US009584931B2

(12) United States Patent
Kohl et al.

(10) Patent No.: US 9,584,931 B2
(45) Date of Patent: Feb. 28, 2017

(54) MIDDLE EAR IMPLANTABLE MICROPHONE

(71) Applicant: MED-EL Elektromedizinische Geraete GmbH, Innsbruck (AT)

(72) Inventors: Franz Kohl, Brunn am Gebirge (AT); Wilfried Hortschitz, Pöttsching (AT); Matthias Sachse, Wiener Neustadt (AT); Thilo Sauter, Vienna (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 13/776,967

(22) Filed: Feb. 26, 2013

(65) Prior Publication Data

US 2013/0170681 A1 Jul. 4, 2013

Related U.S. Application Data

(63) Continuation of application No. PCT/US2011/050280, filed on Sep. 2, 2011.

(Continued)

(51) Int. Cl.

*H04R 25/00* (2006.01)
*H04R 19/04* (2006.01)

(Continued)

(52) U.S. Cl.

CPC ............ *H04R 25/50* (2013.01); *H04R 19/04* (2013.01); *H04R 25/604* (2013.01);

(Continued)

(58) Field of Classification Search

USPC .......................................................... 381/320

See application file for complete search history.

(56) References Cited

U.S. PATENT DOCUMENTS 5,772,575 A 6/1998 Lesinski et al. ................ 600/25
5,879,283 A 3/1999 Adams et al. .................. 600/25

(Continued)

FOREIGN PATENT DOCUMENTS

WO WO 2009/079021 6/2009 ............. H04R 19/01

OTHER PUBLICATIONS

Rodriguez et al., "Laser vibrometry: A middle ear and cochlear analysis tool for the non-invasive diagnosis of middle ear and cochlear pathologies," ENT, vol. 25, pp. 997-1007, 1997 (In German).

(Continued)

*Primary Examiner* — Amir Etesam

(74) *Attorney, Agent, or Firm* — Sunstein Kann Murphy & Timbers LLP

(57) ABSTRACT

A method of sensing vibrations in the middle ear is presented. The method includes implanting a transducer in the middle ear. The transducer measures vibration, within a predetermined frequency range, of at least one component of the middle ear. The transducer has a resonance frequency within the predetermined frequency range, and further has a limited frequency response in a portion of the frequency range. The implanting includes operatively coupling the implant to the at least one component of the middle ear such that the limited frequency response of the transducer is complimentary to, and compensated by, the frequency characteristics of the at least one component of the middle ear.

14 Claims, 12 Drawing Sheets

Related U.S. Application Data

(60) Provisional application No. 61/379,833, filed on Sep. 3, 2010.

(51) Int. Cl.
*H04R 31/00* (2006.01)
*A61N 1/36* (2006.01)
*H04R 3/06* (2006.01)

(52) U.S. Cl.
CPC .......... *H04R 31/00* (2013.01); *A61N 1/36032* (2013.01); *H04R 3/06* (2013.01); *H04R 25/606* (2013.01); *H04R 2201/003* (2013.01); *H04R 2225/67* (2013.01); *H04R 2410/03* (2013.01); *H04R 2430/03* (2013.01)

(56) References Cited

U.S. PATENT DOCUMENTS

| | | | | |
|---|---|---|---|---|
| 5,954,628 | A | 9/1999 | Kennedy | 600/25 |
| 6,068,589 | A | 5/2000 | Neukermans | 600/25 |
| 6,216,040 | B1 | 4/2001 | Harrison | 607/57 |
| 6,342,035 | B1 | 1/2002 | Kroll et al. | 600/25 |
| 6,712,754 | B2 | 3/2004 | Miller et al. | 600/25 |
| 6,788,796 | B1 | 9/2004 | Miles et al. | 381/357 |
| 7,104,130 | B2 * | 9/2006 | Kenny | B81B 7/0077 600/25 |
| 7,582,052 | B2 | 9/2009 | Waldmann | 600/25 |
| 2002/0026091 | A1 | 2/2002 | Leysieffer | 600/25 |
| 2002/0176594 | A1 * | 11/2002 | Hohmann | H04R 25/407 381/312 |
| 2005/0137447 | A1 | 6/2005 | Bernhard | 600/25 |
| 2005/0245990 | A1 | 11/2005 | Roberson | 607/57 |
| 2011/0142274 | A1 * | 6/2011 | Perkins | H04R 25/606 381/328 |
| 2012/0215055 | A1 * | 8/2012 | Van Vlem | H04R 25/606 600/25 |

OTHER PUBLICATIONS

Rodriguez et al., "Laser vibrometry: A middle ear and cochlear analysis tool for the non-invasive diagnosis of middle ear and cochlear pathologies," ENT, vol. 25, pp. 997-1007, 1997 (English translation).

Schwab, Defining normal values for acoustically triggered tympanic membrane vibrations by means of laser Doppler interferometry, Thesis, Zurich University Hospital Clinic and Polyclinic for Oto-rhinolaryngology, Head and Neck Surgery Director: Prof Dr. med S. Schmid, 52 pages. ( In German).

Schwab, Defining normal values for acoustically triggered tympanic membrane vibrations by means of laser Doppler interferometry, Thesis, Zurich University Hospital Clinic and Polyclinic for Oto-rhinolaryngology, Head and Neck Surgery Director: Prof Dr. med S. Schmid, 52 pages (English translation).

Ko et al., "MEMS Acoustic Sensors for Totally Implantable Hearing Aid Systems," IEEE, pp. 1812-1817, 2008.

Park et al., "Ultraminiature encapsulated accelerometers as a fully implantable sensor for implantable hearing aids," Biomed Microdevices, vol. 9, pp. 939-949, 2007.

Young et al., "Implantable MEMS Accelerometer Microphone for Cochlear Prosthesis," 4 pages.

International Searching Authority, International Search Report—International Application No. PCT/US2011/050280, dated Dec. 28, 2011, together with the Written Opinion of the International Searching Authority, 10 pages.

* cited by examiner

MIDDLE EAR IMPLANTABLE MICROPHONE

CROSS-REFERENCE TO RELATED APPLICATIONS

This application is a continuation of Patent Cooperation Treaty Application PCT/US2011/050280, filed Sep. 2, 2011, which in turn claims priority from U.S. provisional application Ser. No. 61/379,833, entitled "Middle Ear Implantable Microphone," filed Sep. 3, 2010, each of which are hereby incorporated herein by reference in its entirety.

TECHNICAL FIELD

The present invention relates to an implantable microphone sensor useable with a cochlear implant or hearing aid, and more particularly to an implantable microphone that coupled to a structure within the middle ear.

BACKGROUND ART

FIG. 1 shows the anatomy of a normal human ear. A normal ear transmits sounds through the outer ear 101 to the tympani membrane (i.e., the eardrum) 102, which moves the bones of the middle ear 103, which in turn excites the cochlea 104. The cochlea (or inner ear) 104 includes an upper channel known as the scala vestibuli 105 and a lower channel known as the scala tympani 106, which are connected by the cochlear duct 107. In response to received sounds the stapes, a bone of the middle ear 103, transmits vibrations via the fenestra ovalis (oval window), to the perilymph of the cochlea 104. As a result, the hair cells of the organ of Corti are excited to initiate chemi-electric pulses that are transmitted to the cochlear nerve 113, and ultimately to the brain.

Some patients may have partially or completely impaired hearing for reasons including: long term exposure to environmental noise, congenital defects, damage due to disease or illness, use of certain medications such as aminoglycosides, or physical trauma. Hearing impairment may be of the conductive, sensorineural, or combination types.

One type of implant for patients with impaired hearing yet a fully functioning tympanic membrane and middle ear component(s) is a hearing implant that includes an implantable middle ear microphone. The middle ear microphone detects "sound" by sensing motion of middle ear component(s). The sensed motion of the middle ear may, for example, be processed by an implanted sound processor/cochlear stimulator into stimulus signals. The stimulus signals are adapted to stimulate nerves within the inner ear via a plurality of electrodes in an electrode array positioned in the inner ear (e.g., similar to an electrode array of a traditional cochlear implant).

Classical designs of a middle ear microphone have a resonance frequency that is outside the measured frequency range. In this manner, a flat transfer function across the measured frequency range may be obtained. An exemplary middle ear microphone attached to the umbo of the middle ear is described by Wen H. Ko, J. Guo, Xuesong Ye, R. Zhang, D. J. Young, *MEMS Acoustic Sensor for Totally Implantable Hearing Aid Systems*, IEEE Transactions on Biomedical Circuits and Systems, Volume 3, Issue 5, p. 277-285, 2008, which is hereby incorporated herein by reference in its entirety. The microphone disclosed by Ko et al. has a limited low frequency measurement range, being designed to work from 250 Hz to 8 KHz, and has a resonance frequency outside the used measurement range (200 Hz). The type of microphone disclosed by Ko et al. is an electrets microphone. Hence low frequencies below 200 Hz cannot be measured well. It also suffers from a large electrostatic force introduced by the electrets.

Another middle ear microphone design is disclosed in Darrin J. Young, Mark A. Zurcher, Wen H. Ko, Maroun Semaan, Cliff A. Megerian, *Implantable MEMS Accelerometer Microphone for Cochlear Prosthesis*, IEEE International Symposium on Circuits and Systems, ISCAS 2007, pages 3119-3122, 2007, which is hereby incorporated herein by reference in its entirety. The microphone of Young et al., is attached to the umbo of the middle ear, and is designed as an accelerometer (as opposed to a seismic sensor), with a targeted resonance frequency of 10 kHz. As the targeted frequency range is below 10 kHz, the microphone in Young et al. appears to be designed as a low pass filter, which is consistent with their description of the microphone as an accelerometer. Due to the high resonance frequency, the microphone of Young et al., is very limited in the low frequency range Still another middle ear microphone is disclosed by Woo-Tae Park et al., *Ultraminiature Encapsulated Accelerometers as a Fully Implantable Sensor for Implantable Hearing Aids*, Biomed Microdevices, 9:939-9:949, 2007, which is hereby incorporated herein by reference in its entirety. The microphone disclosed by Woo-Tae Park et al. is a piezo-resistive microphone fixed at the stapes of the middle ear. Similar to the microphone of Young et al., the microphone is designed as an accelerometer (as opposed to a seismic sensor) with a resonance frequency in the range of 6 kHz. Due to the high resonance frequency, measurements are possible in the range of 900 Hz to 10 kHz, but are too limited in lower frequencies

SUMMARY OF THE INVENTION

In accordance with a first embodiment of the invention, a method of sensing vibrations in the middle ear is presented. The method includes implanting a transducer in the middle ear. The transducer measures vibration, within a predetermined frequency range, of at least one component of the middle ear. The transducer has a resonance frequency within the predetermined frequency range, and further has a limited frequency response in a portion of the frequency range. The implanting includes operatively coupling the implant to the at least one component of the middle ear such that the limited frequency response of the transducer is complimentary to, and compensated by, the frequency characteristics of the at least one component of the middle ear.

In accordance with another embodiment of the invention, a method of optimizing a hearing implant is provided. The hearing implant includes a transducer for measuring vibration, within a predetermined frequency range, of the at least one component of the middle ear. The method includes providing a resonance frequency of the middle ear transducer to be within the predetermined frequency range, the transducer having a limited frequency response in a portion of the predetermined frequency range. When the transducer is operatively coupled to the at least one component of the middle ear, the limited frequency response of the transducer is complimentary to, and is compensated by, the frequency characteristics of the at least component of the middle ear.

In accordance with another embodiment of the invention, a system for sensing vibrations in the middle ear is presented. The system includes a transducer for measuring vibration, within a predetermined frequency range, of at least one component of the middle ear. The transducer has a resonance frequency within the frequency range, and further has a limited frequency response in a portion of the frequency range. An attachment mechanism is provided for attaching the transducer to the at least one middle ear component. When the transducer is operatively coupled to the at least one component of the middle ear, the limited frequency response of the transducer is complimentary to, and compensated by, the frequency characteristics of the at least component of the middle ear.

In accordance with embodiments related to the above-described embodiments, the resonance frequency may be between 300 Hz to 4.5 kHz. The resonant frequency may be between 500 Hz to 2.5 kHz. The predetermined frequency range may be between 100 Hz to 10 kHz. The transducer may act as a seismic sensor with high pass filter characteristics, and have a limited frequency response in the low frequency range, the low frequency range being one of between 100 Hz to 300 Hz, between 100 Hz to 500 Hz, between 100 Hz to 1000 Hz, between 100 Hz to 2.5 kHz, and between 100 Hz to 4.5 KHz.

In accordance with further related embodiments of the invention, signal processing may be performed on the measured vibration. The measured vibration may be filtered with a notch filter to flatten the frequency response of the transducer at the resonance frequency. The output of the transducer may be processed via a plurality of frequency channels. The resonance frequency may be determined as a function of mechanical thermal noise associated with each channel. For example, determining the resonance frequency may be based on ensuring that the mechanical thermal noise in each channel is below the relative movement of the transducer when operatively coupled to the at least one component of the middle ear. Determining the resonance frequency may include optimizing the transducer to maximize the resonance frequency as a function of a predetermined transducer mass. Determining the resonance frequency may be a function of static deflection (static deflection is the displacement of the transducer caused by gravity). For example, determining the resonance frequency may be based, at least in part, on minimizing static deflection of the transducer when operatively coupled to the at least one component of the middle ear. The system and method may further include providing a stimulation signal to at least one electrode in an electrode array based on the processed signal within the cochlea to provide perception of sound. The resonance frequency of the transducer may be determined such that when the transducer is operatively coupled to the at least one component of the middle ear, the transducer has an output optimized to provide a low signal dynamic. The at least one component of the middle ear may include the umbo, the processus lenticularis and/or the stapes.

BRIEF DESCRIPTION OF THE DRAWINGS

The foregoing features of the invention will be more readily understood by reference to the following detailed description, taken with reference to the accompanying drawings, in which:

FIG. 5(*b*) shows a PT2 system transfer function over various resonance frequencies.

FIG. 6(*b*) shows a footpoint excited system where the excitation frequency is above the resonance frequency.

FIG. 6(*c*) shows a footpoint excited system where the excitation frequency is below the resonance frequency.

FIG. 7(*b*) shows an excitation signal for an inertial transducer acting as a seismic sensor.

FIG. 9(*b*) shows the capacitive change of a differential capacitive sensor when the overall capacity of both parts is compared.

DETAILED DESCRIPTION OF SPECIFIC EMBODIMENTS

In illustrative embodiments, a middle ear implantable microphone acting as a seismic sensor with high pass filter characteristics (as opposed to an accelerometer), and having a resonance frequency within a predetermined operating frequency range of, without limitation, between 100 Hz and 10 kHz, is described. Selecting such a resonance frequency enables the microphone device to have some favourable parameters, such as a very low mass of the vibration detecting unit. Possible disadvantages of a non-flat frequency characteristic in the operating range of the microphone are compensated by the entire micro system environment comprising both the anatomical and functional structure of the ear from tympanic membrane to the brain and the implantable microphone itself. Details are described below.

For the design of an implantable middle ear microphone, the following three boundary conditions become important.

Figure 1:
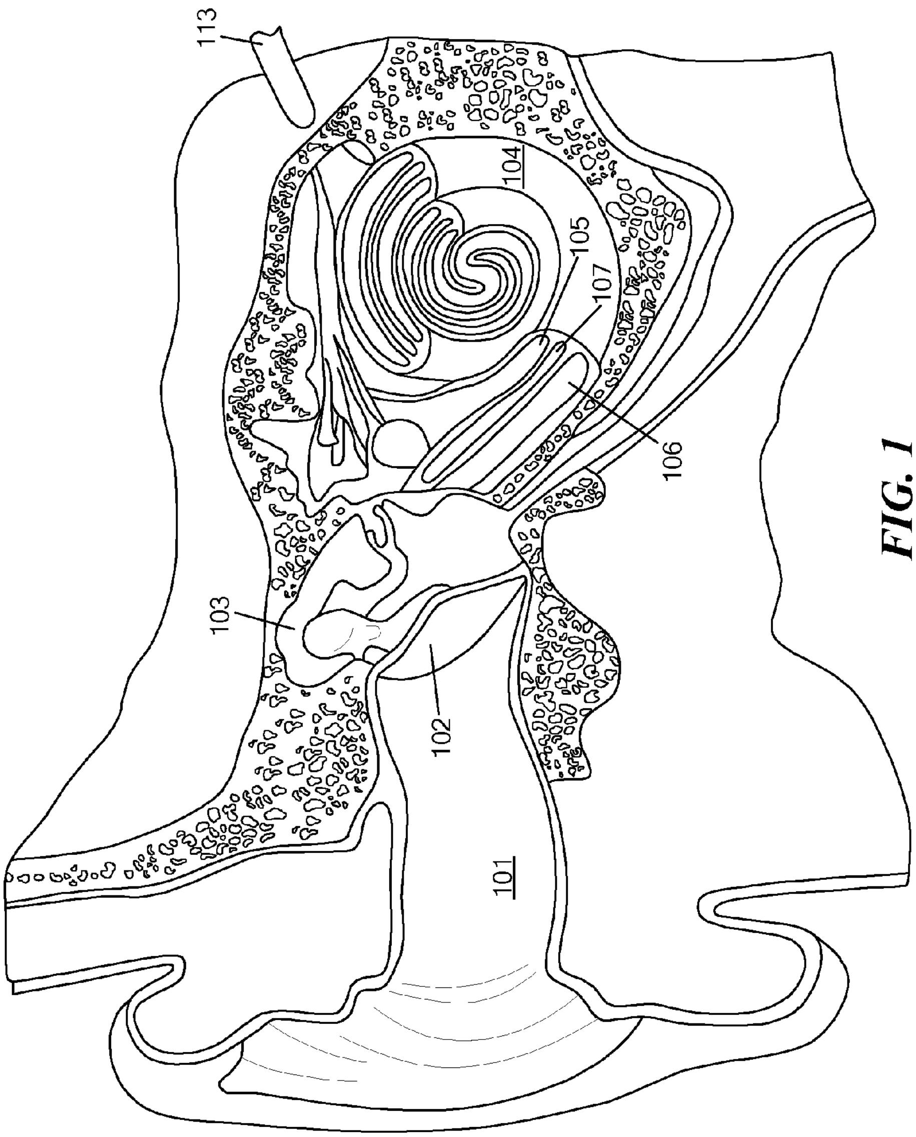
FIG. 1 shows the anatomy of a normal human ear.
Figure 2:
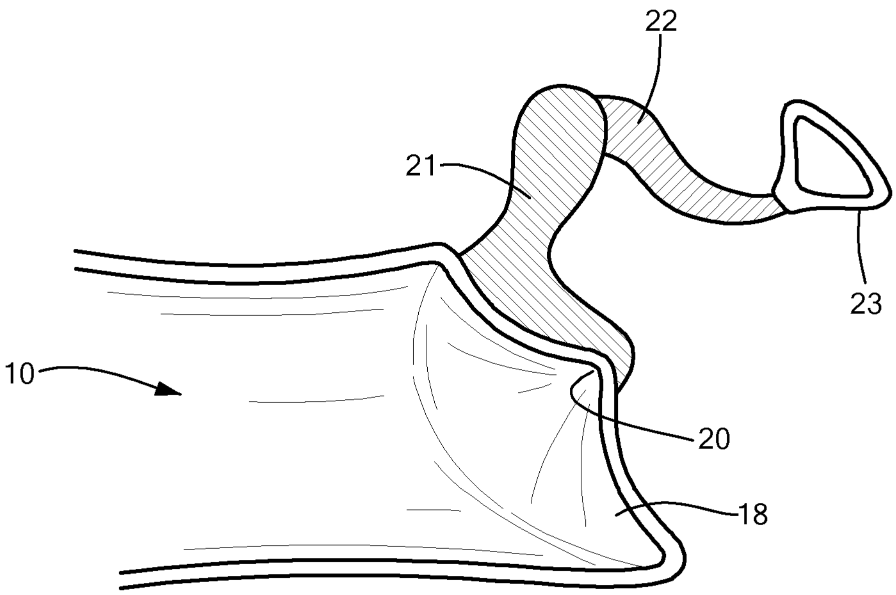
FIG. 2 shows a side view of the middle ear.

1. The Ossicle Chain Deflection Over Frequency and the Physiology of the Auditory System FIG. 2 shows a side view of the middle ear. The ear canal 10 leads to the tympanic member 18 (i.e., the eardrum). The tympanic membrane is connected to the malleus ossicle 21, which in turn is connected to the incus 22, which in turn is connected to the stapes 23 within the middle ear. Sound entering the ear canal 10, vibrates the tympanic bone, leading to vibrations in the ossicle chain (i.e., the malleus ossicle 21, the incus 22 and the stapes 23). As the middle ear works as an impedance converter, the ossicle deflections are larger at the ear drum 18 than at the stapes 23 footplate. Hence, the ideal position for the transducer is at the umbo 20, the connection point of ear drum and ossicle chain. The umbo 20 is also well reachable for surgeons.

Figure 3:
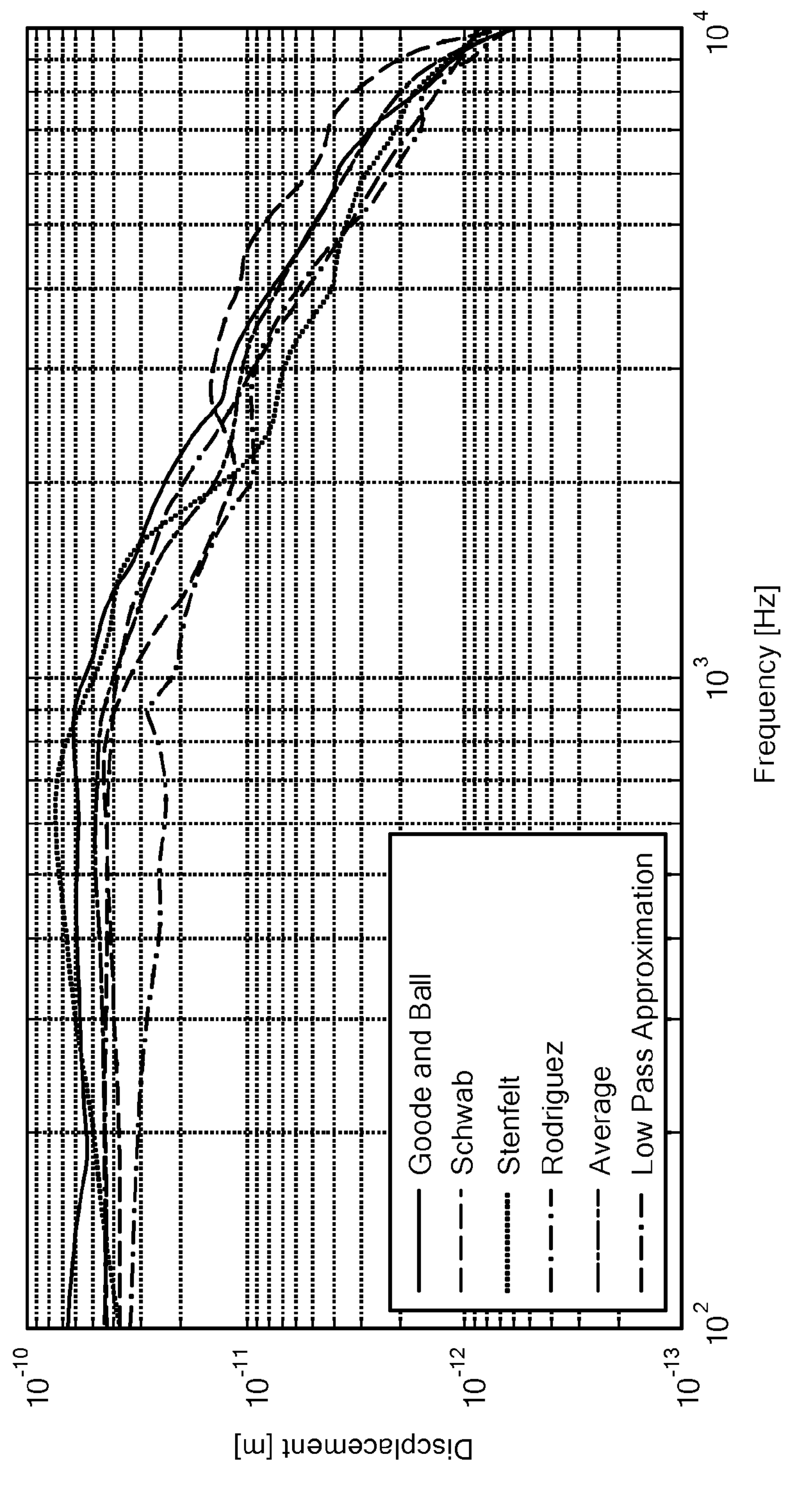
FIG. 3 shows umbo deflection over frequency with an excitation of 30 dB SPL.

The umbo deflection over frequency is shown in FIG. 3. Several displacement measurements of the umbo are shown, normalized to 30 dB SPL. The measurement of Goode and Ball were performed with 84 dB SPL (R. Goode, G. Ball, et al., *Laser Doppler vibrometer* (*LDV*)—*A new clinical tool for the Ontologist, Am-J. Otol,* 17, 813-8223, 1996); Rodriguez with 60 dB SPL (J. Rodriguez, Laser vibrometry. *A Middle Ear and Cochlear Analyzer for Noninvasive Studies of Middle and Inner Ear Function Disorders*, HNO. December; 45(12):997-1007, 1997); Schwab with 80 dB SPL (C. G. Schwab, *Normalwertbestimmung von akustisch ausgelosten Trommelfell-Schwingungen mittels*, Laser Doppler Interferometrie, Dissertation Universitatsspital Zurich, 2002); and Stenfelt also with 80 dB SPL (S. Stenfelt, *Middle Ear Ossicles Motion at Hearing Tresholds with Air Conduction and Bone Conduction Stimulation*, J. Acoust. Soc. Am, Vol 119, Issue 5, Pages 2848-2858, 2005), each of which is hereby incorporated herein by reference in their entirety. In combination with the microphone, the A-Rating (see http://www.itu.int/publ/R-REC/en) has to be taken into account, or the more advanced IS0226 (2003) Rating (see http://www.iso.org/iso/iso_catalogue/catalogue_tc/catalogue_detail.htm?csnumber=34222), each of which is hereby incorporated herein by reference in their entirety. The latter one represents the hearing threshold and loudness contours more accurate then the A-Rating.

Figure 4:
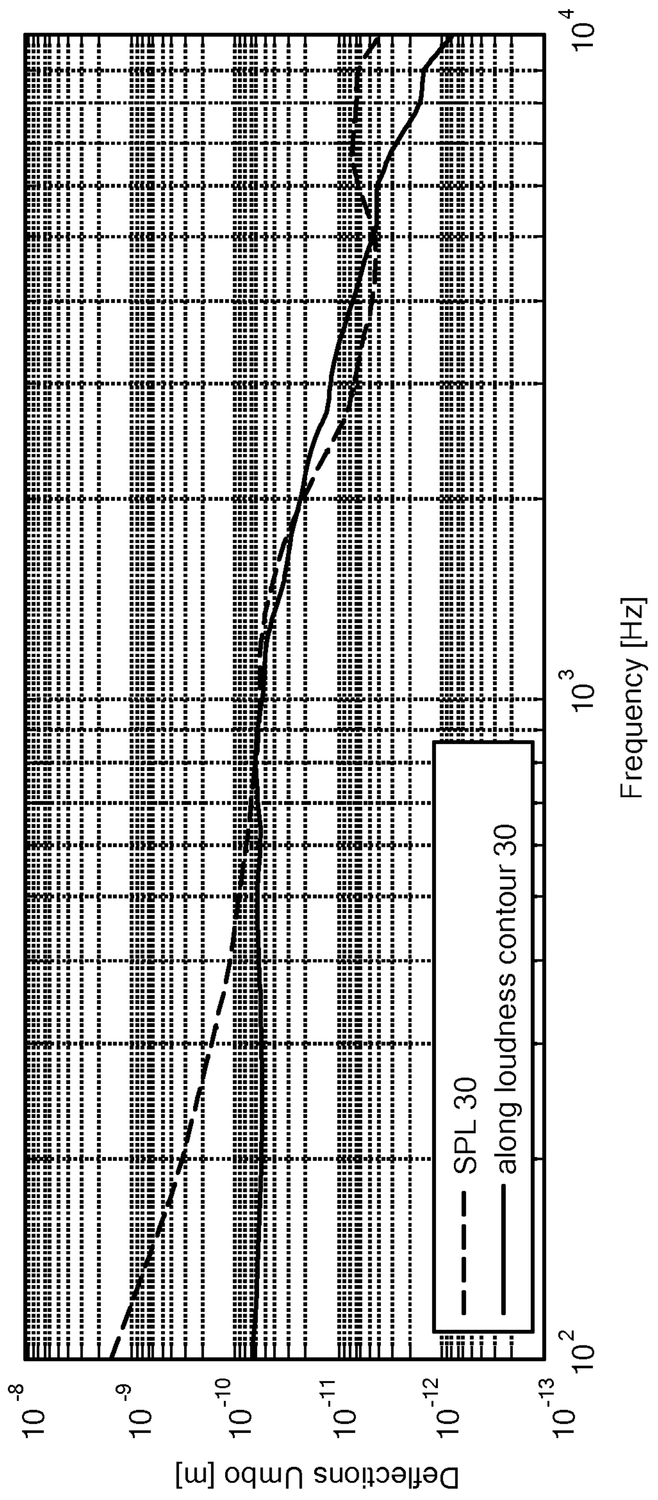
FIG. 4 shows the comparison of rated (dashed line) and unrated deflection curve of the umbo.

If the deflection of the umbo is rated with the loudness contour (e.g., at 30 dB SPL) the resulting deflection curve is much different from the unrated one. FIG. 4 shows the comparison of rated and unrated deflection curve of the umbo. Remarkable is the large deflection difference between the high and the lower frequencies. A transducer would have to cover more than two magnitudes of signal dynamics just within on level of the loudness contour.

2. The Measurement Range and the Resonance Frequency of the Transducer

To measure the incoming sound with a fully implantable middle ear microphone, the transducer has to measure the vibrations of the bone (i.e., a seismic sensor). The transfer function for such a transducer, assuming one degree of freedom due to one measurement direction and one relevant eigenfrequency, is $$G(j\omega_e) = \frac{X_{rel}(j\omega_e)}{Y(j\omega_e)} = \frac{\omega_e^2}{(j\omega_e)^2 + 2\vartheta(j\omega_e) + w_0^2}$$

where $\omega_e$ is the circular frequency of the excitation, is the damping constant/(2 mass), $X_{rel}$ is the amplitude of the relative movement, and Y is the amplitude of the input deflection.

Figure 5A:
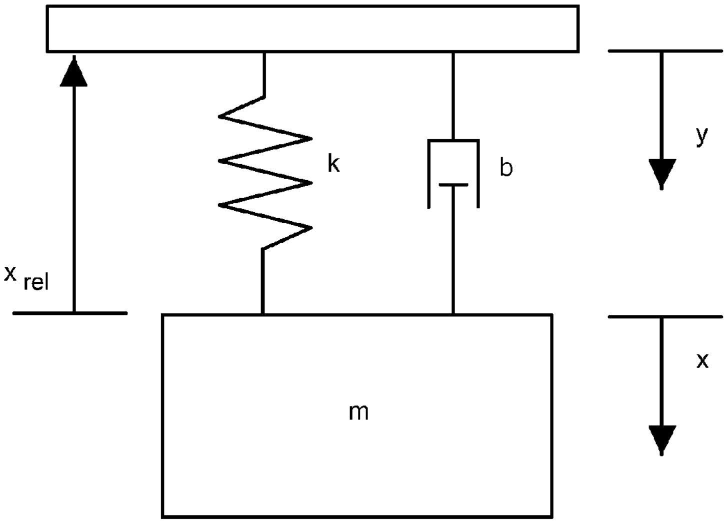
FIG. 5(*a*) shows a schematic of a footpoint excitated system (i.e., a seismic sensor).
Figure 5B:
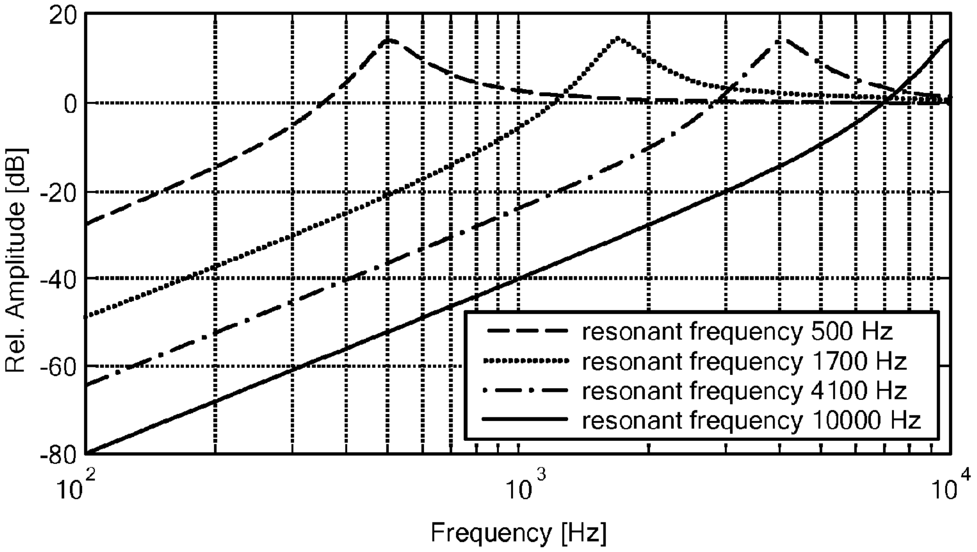

In system theory, this is called PT2 system transfer function. A schematic of an footpoint excited system acting as a seismic sensor is shown in FIG. 5(*a*), in which $X_{REL}$ is measured. The PT2 system transfer function over various resonance frequencies is plotted in FIG. 5(*b*). A higher resonance frequency leads to a lower sensitivity in the lower frequency range.

Figure 6B:
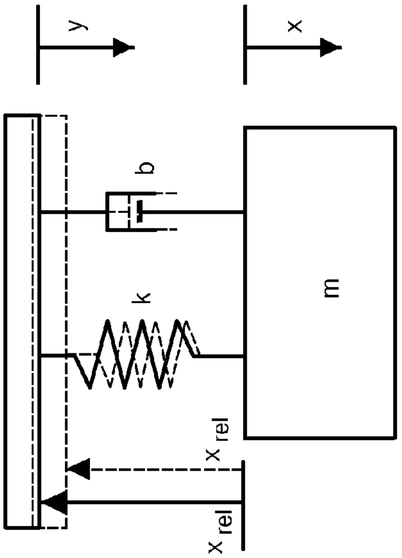
FIG. 6(*a*) shows a mass excited system (i.e. an accelerometer) when the excitation frequency is below the resonance frequency of the system.
Figure 6C:
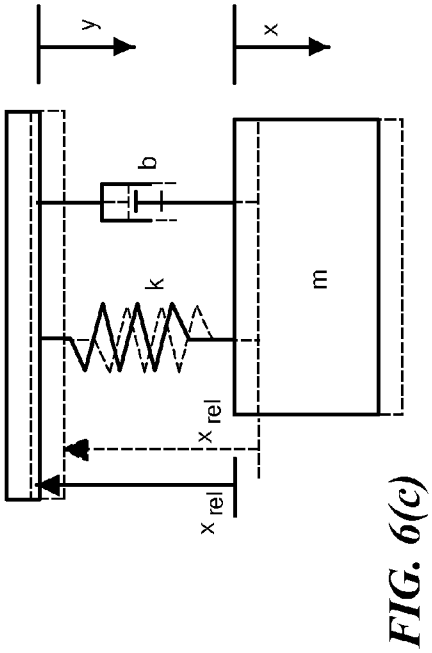
Figure 6A:
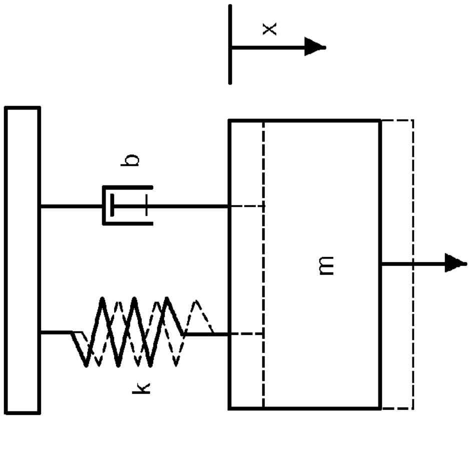

FIG. 6(*a*) shows a mass excited system (i.e. an accelerometer) when the excitation frequency is below the resonance frequency of the system. Here the top plate is fixed and the mass m is moving back and forth. The top plate can be regarded as the implant housing with the mass fixed to the housing via springs with a spring constant c. The mass m can follow the excitation force (blue shape). If the frequency is above the resonance frequency, the mass cannot follow the excitation (black shape).

However, the housing of the proposed middle ear microphone is attached to the vibrating umbo in the middle ear, and is not fixed. Therefore, a schematic drawing of a MEMS sensor attached to the middle ear is a footpoint excited system (i.e., a seismic sensor) shown in FIGS. 6(*b*) and 6(*c*) (see also FIG. 5(*a*)). FIG. 6(*b*) shows a footpoint excited system where the excitation frequency is above the resonance frequency. The mass cannot follow the excitation. Hence a relative movement of the mass compared to the footpoint can be measured. FIG. 6(*c*) shows a footpoint excited system where the excitation frequency is below the resonance frequency. The mass can follow the excitation. Hence, there is no relative movement between mass and footpoint.

Figure 7A:
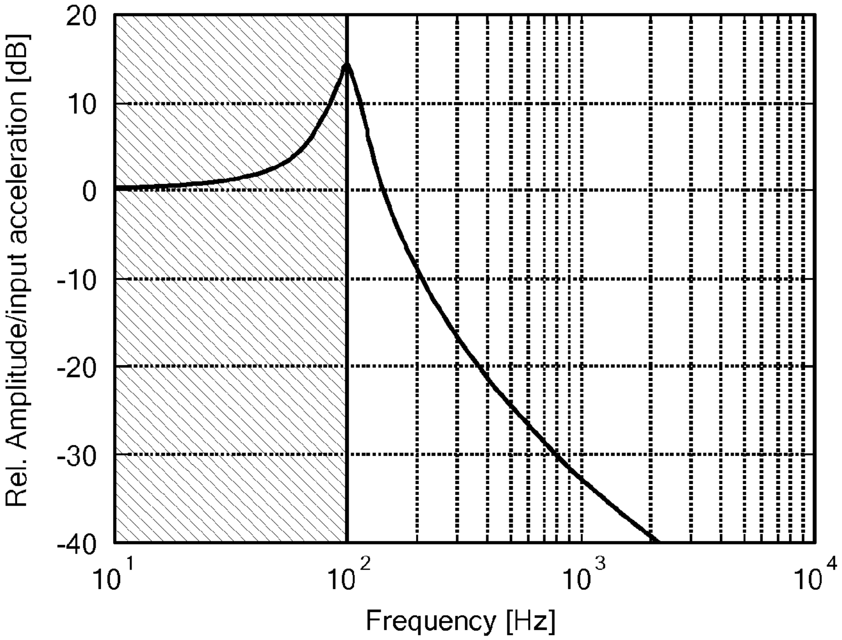
FIG. 7(*a*) shows an excitation signal for an inertial transducer acting as an accelerometer.
Figure 7B:
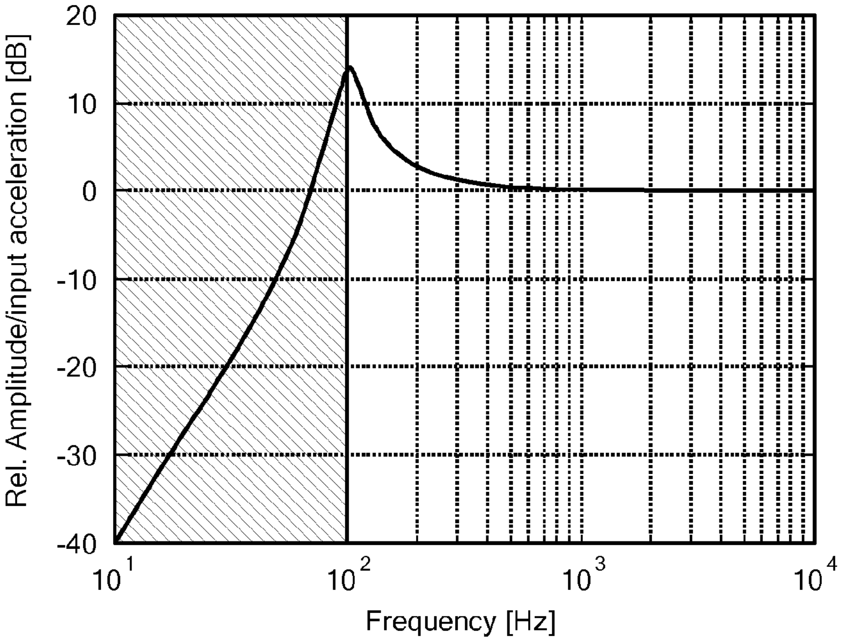

FIGS. 7(*a*) and 7(*b*) show the two excitation signals for a inertial transducer acting as an accelerometer and seismic sensor, respectively. The accelerometer has low pass filter characteristics, while the seismic sensor has high pass filter characteristics. For example, as shown in FIG. 7(*b*), the seismic sensor acting as a high pass filter may include a limited frequency response at lower than its associated cut-off frequency. In illustrative embodiments, the transducer may have a limited frequency response in the low frequency range, the low frequency range being, with limitation, between 100 Hz to 300 Hz, between 100 Hz to 500 Hz, between 100 Hz to 1000 Hz, between 100 Hz to 2.5 kHz or between 100 Hz to 4.5 KHz The PT2 system may not only react to vibrations, but also to acceleration. This is a big disadvantage because these accelerations can cause transducer signals more than 5 magnitudes larger than the vibration of the bones. This must be suppressed. Fortunately, the lower frequencies are not included in a cochlear implant stimulation. Hence, these frequencies can be filtered. However, such filtering often may not occur until after the first amplifier, which is a big drawback for the sensitivity of the circuit. It may be more efficient to suppress the acceleration, for example, with a larger resonance frequency, or build a control loop for the sensor. The latter choice needs more energy so the choice of a higher resonance frequency may be advantageous for the power consumption. But due to the fact that the resonance frequency cannot be raised unlimited, a mix of a higher resonance frequency and a control loop may be preferable.

The acceleration which is often most distracting is the gravitational acceleration. This acceleration can be considered as static. Even for head rotation this assumption is valid due to the very low frequency of the rotation. The static acceleration causes a static deflection of the transducer which causes a signal offset. The static deflection of a transducer can be calculated with the equation deflection=acceleration/(angular resonance frequency)$^2$. That means 25 μm static deflections (e.g. through head-turning) for a system with an angular resonance frequency of 100 Hz. With this big offset it is hardly possible to detect the 5 pm deflection of the umbo at 30 dB SPL.

3. The Available Space at the Fixing Position and the Access for the Surgeon

The umbo is best suited due to its large deflection and its space for fixing and placing an implantable device. Also the access for the surgeon seems to be (easily) possible.

Illustratively, the middle ear microphone may be, without limitation, a differential capacitive transducer. Other types of microphones known in the art may be utilized (particularly MEMS microphones due to their small size) and are within the scope of the present invention. Because the space in the middle ear is limited, the overall size of the microphone housing (including sensor, electronics and sensor housing, but without connecting electronic wiring) itself must be very small (typically in the range of 1×1×1 mm to 3.5×3.5×3.5 mm, preferably between 2×2×1 mm to 3×3×2 mm). Also, to avoid high stress on the ossicles and as a consequence a mistuning of the chain, the complete system typically should, without limitation, not exceed 50 mg A preferable range for the overall mass of the microphone housing (including sensor, electronics and sensor housing, but without connecting electronic wiring) would be 5-50 mg, more preferably 10-30 mg.

Figure 8:
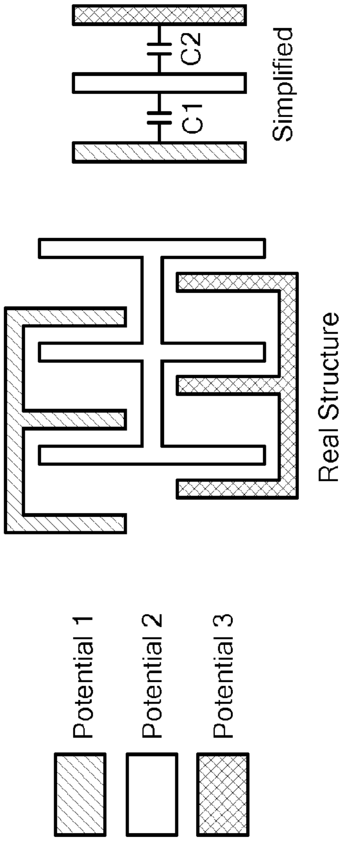
FIG. 8 shows a schematic of a differential capacitive transducer.

FIG. 8 shows a schematic of the differential capacitive transducer, in accordance with an embodiment of the invention. The real structures approximates the real geometry of sensor, while the simplified one is sufficient for the calculation and simulation. When potential 2 is moving, the capacities C1 and C2 are changing. One is getting smaller, one larger. For small deflection <10% of gap size, the signal is nearly linear due to the differential measurement principles. The gap size in a capacitive MEMS is very small. This leads to a higher damping. Hence the package of the MEMS may be filled with a rarefied gas under a specific pressure of (e.g. 10-50000 Pa) that leads to a optimal damping ratio of around 0.707. This Damping ratio is preferable because it has the fast signal response without a large overshoot.

Figure 9A:
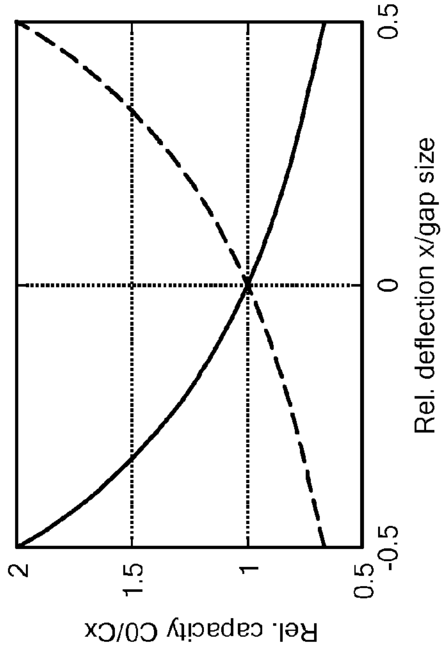
FIG. 9(*a*) shows capacitive change on half of differential capacitive sensor.
Figure 9B:
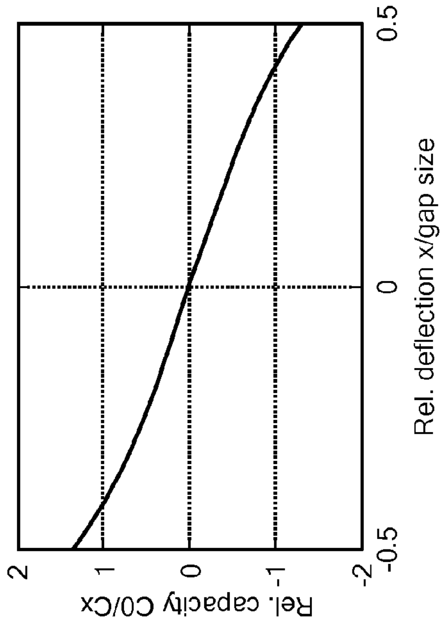

FIG. 9(*a*) shows capacitive change on half of the sensor. The change is not symmetrical, which is cumbersome when using as a sensor. FIG. 9(*b*) shows the capacitive change of the transducer when the overall capacity of both parts is compared. Within a plate distance of 10%, the change is symmetrical. Hence, this concept is preferred for sensor application.

In accordance with various embodiments of the invention, three goals of the implantable microphone design include low static deflection, low thermal noise, and/or a small size. To achieve these goals, the design of the middle ear microphone advantageously considers the umbo deflection, the loudness contour and/or the transfer characteristics of the transducer, in accordance with an embodiment of the invention. The displacement of the umbo at low frequencies (<1 kHz) is significantly higher than at high frequencies (above lkHz, see IDF FIG. 3). Utilizing this anatomical characteristic an optimum resonance frequency may be chosen (for example, and without limitation, between 300 Hz to 4.5 kHz). Thus, in various embodiments of the invention, a resonance frequency is selected that is well within the predetermined measurement range between, without limitation, 100 Hz and 10 kHz.

When using a higher resonance frequency, static deflection decreases and the thermal noise is reduced. The basic mechanical thermal noise can be calculated with the equation sqrt(4 kT/($\omega_0$^3 mQ)). k is the Boltzmann constant, T the temperature, $\omega_0$ the circular eigenfrequency and Q the quality. This is very important because the mechanical thermal noise is one limit of the resolution of the microphone. The thermal noise can be influenced with three parameters: mass, resonance frequency and quality. If the quality is given, only mass and resonance frequency are left to be changed. The mass cannot be raised unlimited because space is limited. Hence, a good way of reducing thermal noise is to raise the resonance frequency. But this is contrary to the transfer function of the transducer, which acts as a high pass filter when acting as a seismic sensor. Fortunately, illustrative embodiments of the invention advantageously take into account that the rated umbo deflection is higher at lower frequencies, such that both effects substantially cancel each other.

In illustrative embodiments of the invention, three optimizing goals are presented below, an accordance with various embodiments of the invention. A short overview is given in table 1.

TABLE ONE

| | Optimization | | |
|---|---|---|---|
| | 1 | 2 | 3 |
| Main Benefit | Optimized Output with lowest possible dynamic and a transfer characteristic which could be flattened with a notch filter | Highest possible resonance frequency with the available mass without violating the detection limit of each channel in a DSP | Highest possible resonance frequency |
| Dependencies | None | Filter bank of the DSP<br>Mass of the transducer | Filter bank of the DSP |
| Precondition | Minimal transducer mass is approximately $2 \times 10^{-7}$ kg<br>One channel | Several channels | Mechanical noise is well below the electrical noise<br>Several channels |

Optimization 1. Reducing the Vibration Signal Dynamics as Much as Possible.

Figure 10:
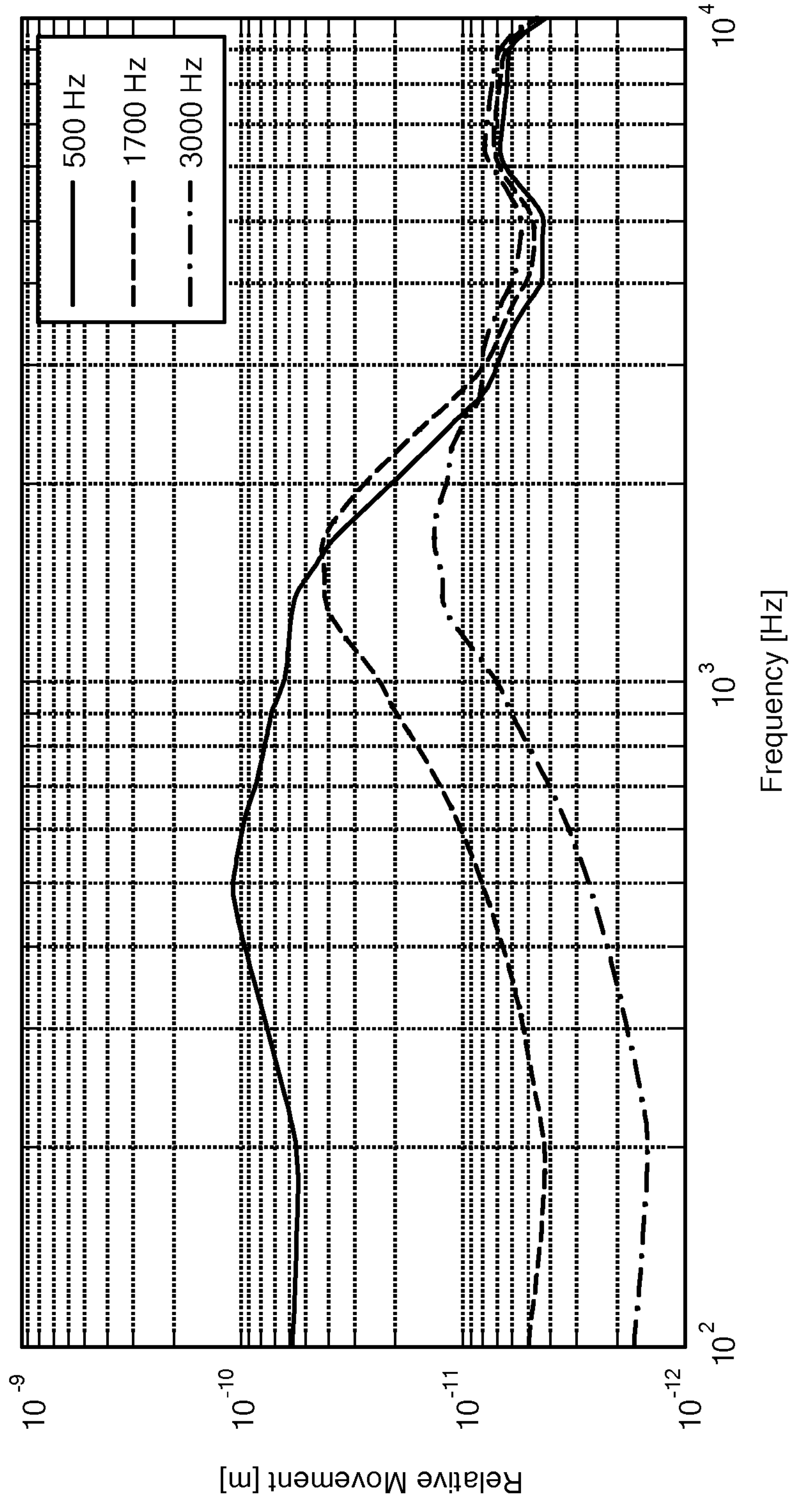
FIG. 10 shows the output of systems having different resonance frequencies when using the umbo deflection along the loudness contour as input, in accordance with various embodiments of the invention.

By taking the ossicle deflection and the loudness contour into account, the resonance frequency may advantageously be raised so as to reduce vibration signal dynamics, in accordance with various embodiments of the invention. FIG. 10 shows the output of systems having different resonance frequencies when using the umbo deflection along the loudness contour as input, in accordance with various embodiments of the invention. The 1700 Hz system has the smallest dynamic of the measurement signal (as the measurement signal has approximately the same magnitude for high and low frequencies). The static deflection of 86 nm is an additional benefit. For 500 Hz the dynamic is a little bit larger and the static deflection is also more than ten times larger. The system with 3000 Hz resonance frequency is suppressing the vibrations in the lower frequency range. Thus, illustratively and without limitation, the resonance frequency of a transducer (for example, with the transducer attached to the umbo, acting as a seismic sensor with high pass filter characteristics) may advantageously be raised to 300 Hz-4.5 kHz for a one channel system in the digital signal processor (DSP), so as to reduce the vibration signal dynamics, in accordance with various embodiments of the invention. A notch filter may be used to remove the relatively large amplitude at resonance.

In systems in which the digital signal processing of the signal received from the microphone occurs substantially in one channel (as opposed to a plurality of channels that each process a different bandwidth of the signal), the lowest relative displacement determines the necessary sensitivity and noise limit. Hence, illustratively for the 1700 Hz resonance system, the deflection at 100 Hz can advantageously be reduced to the lower levels of the 10 kHz frequency so as to reduce the dynamic range. For the system itself, this is not a loss of sensitivity, but a gain of resistivity against gravity.

Furthermore, compared to a system having a 100 Hz resonance frequency (i.e., a resonance frequency outside of the operating range of audible frequencies), static deflection associated with a system having a 1700 Hz resonance frequency is approximately 300 times smaller.

Optimization 2: Reaching the Highest Possible Resonance Frequency while Minimizing the Mechanical Thermal Noise in the Channels of the Digital Signal Processor.

Compared to the one channel DSP system, the necessary sensitivity in a multi-channel DSP system may not be determined by the lowest relative displacement, but by the noise in each channel. In various embodiments, the deflection in the 100-200 Hz Range may be well below the deflection at 10 kHz. But due to the fact that the channel is smaller at 100-200 Hz (just 100 Hz) compared to the one channel system (10 kHz), the noise is ten times smaller (the noise in one channel depends on the square root of the bandwidth in the channel multiplied with the basic noise level). Hence the signal at the lower frequency range can be damped more, but is still detectable. This pertains to mechanical thermal noise. The frequencies above the resonance frequency generally do not suffer from mechanical thermal noise.

Figure 11:
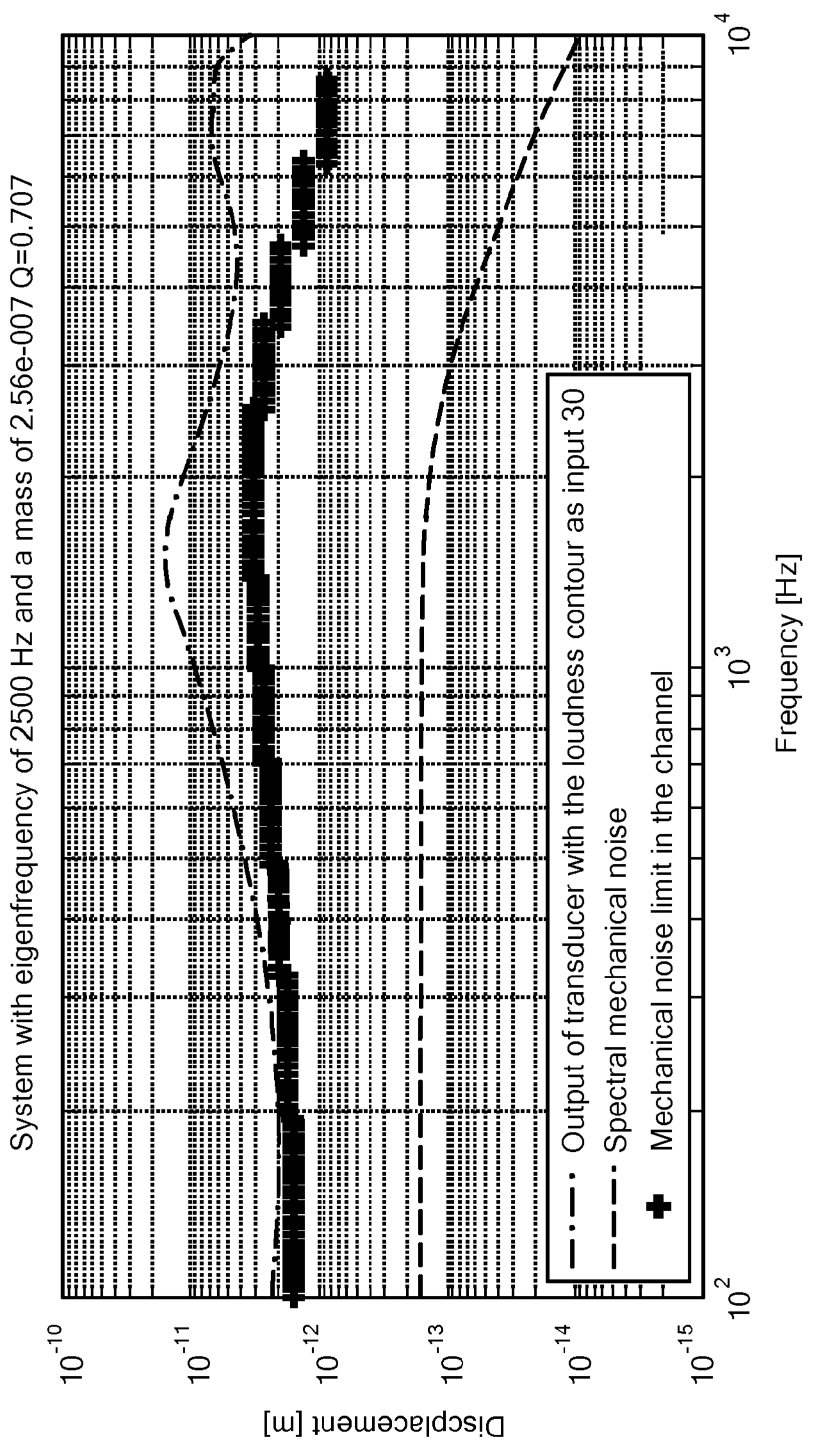
FIG. 11 shows an exemplary multi-channel system with an optimum resonance frequency of 2500 Hz for a DSP filter bank and a MEMS mass of $2\times10^{-7}$ kg, in accordance with an embodiment of the invention.

The spectral mechanical noise has the shape of a lowpass transfer function. With a given mass of the seismic sensor (just the MEMS, not the package), the resonance frequency may be calculated in a way that the mechanical thermal noise in each channel of a multichannel DSP system is below the relative movement of the transducer, in accordance with various embodiments of the invention. This approach is advantageous if the mass of the MEMS is the limiting factor and electronic noise is well below the mechanical noise. FIG. 11 shows an exemplary multichannel system with an optimum resonance frequency of 2500 Hz for a DSP filter bank and a MEMS mass of $2\times10^{-7}$ kg, in accordance with an embodiment of the invention. For a lower mass, the optimum resonance frequency can be lower. If the mass is higher, the resonance frequency can be higher but should not exceed the electrical noise limitation. But a higher mass often may be impractical to implement in MEMS. In accordance with illustrative embodiments of the invention, the mass of the MEMS may be between 200 μg to 2 mg, and more preferably, 250 μg to 1 mg. To increase the mass of the MEMS sensor, special production steps for the deposition of heavy elements may be used, in accordance with various embodiments of the invention. For example, chemical or vapor deposition may be used to deposit heavy elements, such as, without limitation, Tungsten or gold.

Optimization 3: Minimizing the Static Deflection.

Figure 12:
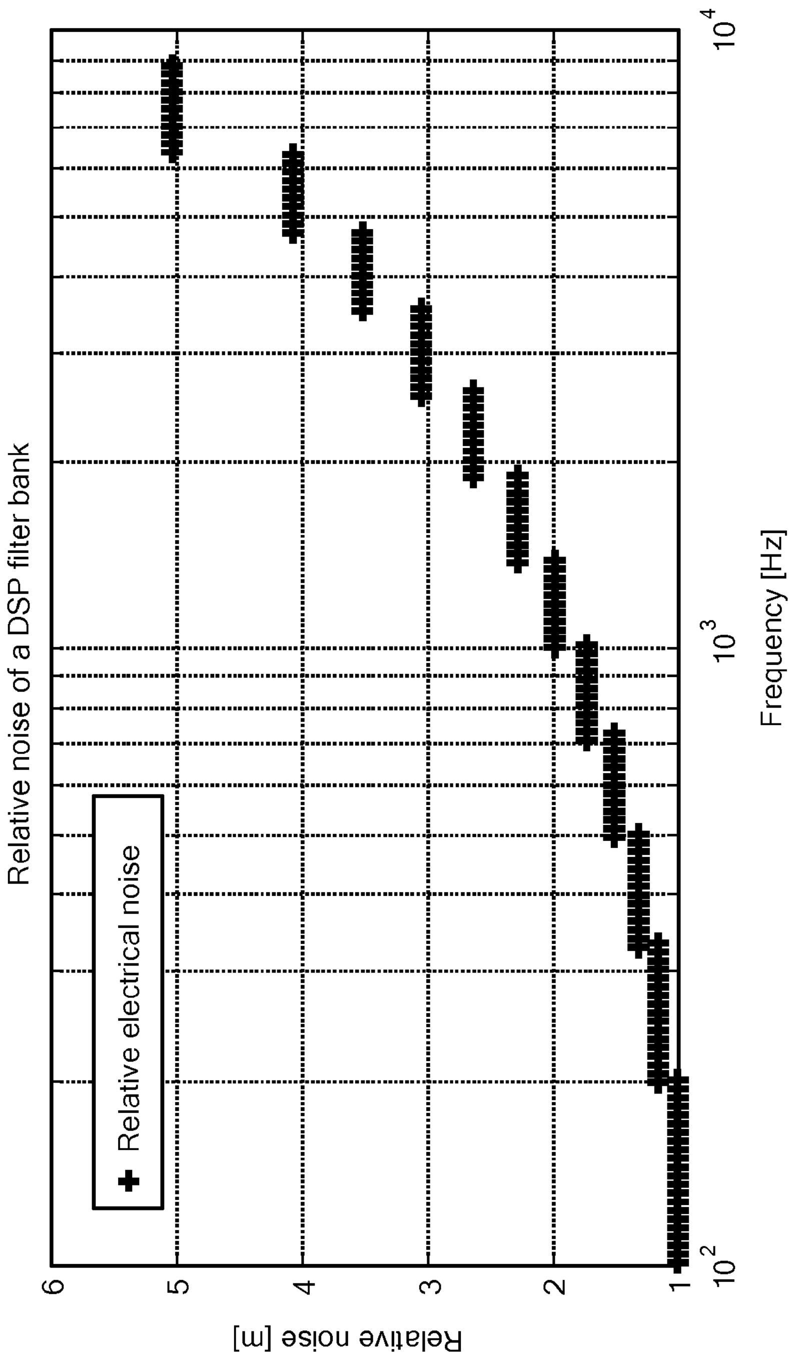
FIG. 12 shows the relative electrical noise of a DSP filter bank, in accordance with an embodiment of the invention.

This approach is advantageous when the mechanical thermal noise is much smaller than the electrical noise and the electrical noise is white. FIG. 12 shows the relative electrical noise of a DSP filter bank, in accordance with an embodiment of the invention.

In this approach, the electrical noise in the smallest channel is compared with electrical noise in the largest. In an exemplary DSP system, the largest channel is 2500 Hz, while the smallest one is 100 Hz (at 100 Hz). That means the noise in the largest channel is 5 times larger than in the smallest channel. So the minimal detectable deflection in the smallest channel is 5 times larger than in the largest one. At 30 dB loudness contour, the static deflection in the 100 Hz channel can be one fifth of the deflection in the higher channel.

Figure 13:
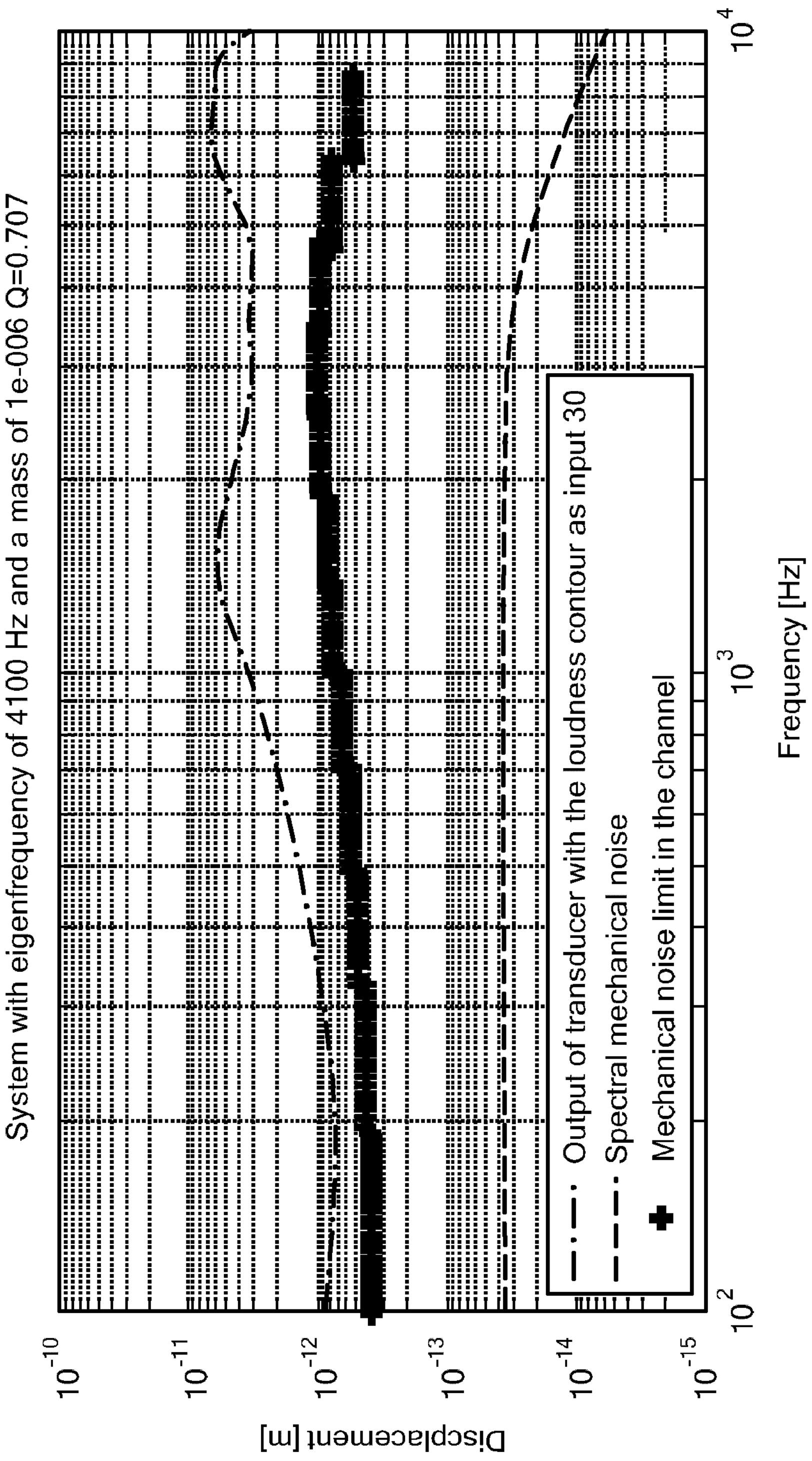
FIG. 13 shows an exemplary multi-channel system with resonance frequency at 4100 Hz, in accordance with various embodiments of the invention

In that case, the resonance frequency can be 4100 Hz, as shown in FIG. 13, in accordance with various embodiments of the invention. This leads to a static deflection of 15 nm. When the resonance frequency is higher, this leads to an even smaller static deflection, but the readout circuit must be more sensitive because the lower frequencies are suppressed too much. This will raise the energy consumption of the system.

CONCLUSION

Without using the optimization as described in the above embodiments of the invention, the resonance frequency of the middle ear microphone has to be much lower. The result would be a very high static deflection. This would result in an over steering of the measurement signal or a reduced sensitivity due to reduced signal amplification.

The higher resonance frequencies associated with the above-described embodiments of the invention allow for stiffer springs. Production of stiffer springs is easier compared to soft ones. Soft springs need lots of space, however, space is limited in the middle ear. Furthermore, production tolerances are higher for soft springs and handling is harder. If the spring is stiffer, the only way to reduce the resonance frequency is increasing mass. But this is difficult due to the limit space. Only special production steps like chemical or physical vapor deposition of Tungsten, Au or other elements can increase the mass significantly. But this is also a risk to the production of the MEMS itself.

State of the Art implantable microphones are not able to measure the whole frequency range due to a much too high resonance frequency, or are limited in their low frequency measurement range. It is crucial to optimize the design regarding the biological boundaries of the middle ear.

The embodiments of the invention described above are intended to be merely exemplary; numerous variations and modifications will be apparent to those skilled in the art. All such variations and modifications are intended to be within the scope of the present invention.

What is claimed is:

1. A method of sensing vibrations of an umbo in the middle ear, the method comprising:

implanting a transducer on the umbo, the transducer for measuring vibration, within a predetermined frequency range of between 100 Hz to 10 KHz, of the umbo, the transducer having a resonance frequency that is between 300 Hz to 4.5 kHz, the transducer acting as a high pass filter having a limited frequency response in a portion of the frequency range below the resonance frequency, wherein implanting includes:

operatively coupling the implant to the umbo such that the limited frequency response of the transducer is complimentary to, and compensated by, the frequency characteristics of the umbo.

2. The method of claim 1, wherein the transducer has a limited frequency response in the low frequency range, the low frequency range being one of between 100 Hz to 300 Hz, between 100 Hz to 500 Hz, between 100 Hz to 1000 Hz, between 100 Hz to 2.5 kHz, and between 100 Hz to 4.5 KHz.

3. The method of claim 1, further comprising filtering the measured vibration with a notch filter to flatten the frequency response of the transducer at the resonance frequency.

4. A method of sensing vibrations in the middle ear, the method comprising:

implanting a transducer in the middle ear, the transducer for measuring vibration, within a predetermined frequency range, of at least one component of the middle ear, the transducer having a resonance frequency within the frequency range, the transducer further having a limited frequency response in a portion of the frequency range, wherein implanting includes:

operatively coupling the implant to the at least one component of the middle ear such that the limited frequency response of the transducer is complimentary to, and compensated by, the frequency characteristics of the at least one component of the middle ear; and performing signal processing on the output of the transducer via a plurality of frequency channels, wherein the resonance frequency is such that the mechanical thermal noise in each channel is below the relative movement of the transducer when operatively coupled to the at least one component of the middle ear.

5. A method of sensing vibrations in the middle ear, the method comprising:

implanting a transducer in the middle ear, the transducer for measuring vibration, within a predetermined frequency range, of at least one component of the middle ear, the transducer having a resonance frequency within the frequency range, the transducer further having a limited frequency response in a portion of the frequency range, wherein implanting includes:

operatively coupling the implant to the at least one component of the middle ear such that the limited frequency response of the transducer is complimentary to, and compensated by, the frequency characteristics of the at least one component of the middle ear; and performing signal processing on the output of the transducer via a plurality of frequency channels, wherein the resonance frequency is provided as a function of mechanical thermal noise associated with each channel, including optimizing the transducer to maximize the resonance frequency as a function of a predetermined transducer mass.

6. The method of claim 1, further comprising providing the resonance frequency so as to minimize static deflection of the transducer when operatively coupled to the umbo.

7. The method of claim 1, wherein the transducer acts as a seismic sensor, for sensing vibration of the umbo and wherein the transducer includes a seismic mass that includes gold and/or tungsten deposited by a chemical and/or a physical vapor deposition.

8. The method of claim 1, further comprising providing the resonance frequency so as to maximizing the resonance frequency as a function of a predetermined transducer mass.

9. A method of optimizing a hearing implant, the hearing implant including a transducer for measuring vibration, within a predetermined frequency range of between 100 Hz to 10 kHz, of an umbo in the middle ear, the method comprising:

providing a resonance frequency of the middle ear transducer that is between 300 Hz to 4.5 kHz, the transducer having a limited frequency response in a portion of the predetermined frequency range below the resonance frequency, such that when the transducer is operatively coupled to the umbo the limited frequency response of the transducer is complimentary to, and compensated by, the frequency characteristics of the umbo, wherein the transducer acts as a high pass filter.

10. The method of claim 9, wherein the transducer has a limited frequency response in the low frequency range, the low frequency range being one of between 100 Hz to 300 Hz, between 100 Hz to 500 Hz, between 100 Hz to 1000 Hz, between 100 Hz to 2.5 kHz, and between 100 Hz to 4.5 KHz.

11. The method of claim 9, wherein the transducer acts as a seismic sensor, for sensing vibration of the at least one component of the umbo, and wherein the transducer includes a seismic mass that includes gold and/or tungsten deposited by one of a chemical and/or a physical vapor deposition.

12. A system for sensing vibrations in an umbo in the middle ear, the method comprising:

a transducer for measuring vibration, within a predetermined frequency range of between 300 Hz to 4.5 kHz, of the umbo, the transducer having a resonance frequency that is between 300 Hz to 4.5 kHz, the transducer acting like a high pass filter and further having a limited frequency response in a portion of the frequency range below the resonance frequency;

an attachment mechanism for attaching the transducer to the umbo;

wherein when the transducer is operatively coupled to the umbo, the limited frequency response of the transducer is complimentary to, and compensated by, the frequency characteristics of the umbo.

13. The system of claim 12, wherein the transducer has a limited frequency response in the low frequency range, the low frequency range being one of between 100 Hz to 300 Hz, between 100 Hz to 500 Hz, between 100 Hz to 1000 Hz, between 100 Hz to 2.5 kHz, and between 100 Hz to 4.5 KHz.

14. The system of claim 12, wherein the transducer includes a seismic mass that includes gold and/or tungsten deposited by a chemical and/or a physical vapor deposition.

* * * * *

UNITED STATES PATENT AND TRADEMARK OFFICE

CERTIFICATE OF CORRECTION

PATENT NO. : 9,584,931 B2
APPLICATION NO. : 13/776967
DATED : February 28, 2017
INVENTOR(S) : Franz Kohl et al.

It is certified that error appears in the above-identified patent and that said Letters Patent is hereby corrected as shown below:

In the Claims

In Column 11, Line 46:
replace “maximizing”
with --maximize--

Signed and Sealed this
Thirtieth Day of May, 2017

Michelle K. Lee

Michelle K. Lee
*Director of the United States Patent and Trademark Office*